(12) United States Patent
Saito (10) Patent No.: US 10,060,897 B2
(45) Date of Patent: Aug. 28, 2018

(54) TANK DEVICE, A VEHICLE, AND A METHOD FOR EVALUATING AN OUTPUT OF A PRESSURE SENSOR

(71) Applicant: TOYOTA JIDOSHA KABUSHIKI KAISHA, Toyota-shi, Aichi-ken (JP)

(72) Inventor: Hiromu Saito, Toyota (JP)

(73) Assignee: Toyota Jidosha Kabushiki Kaisha, Toyota-shi, Aichi-ken (JP)

( * ) Notice: Subject to any disclaimer, the term of this patent is extended or adjusted under 35 U.S.C. 154(b) by 219 days.

(21) Appl. No.: 14/879,834

(22) Filed: Oct. 9, 2015

(65) Prior Publication Data

US 2016/0116450 A1    Apr. 28, 2016

(30) Foreign Application Priority Data

Oct. 24, 2014   (JP) .................................. 2014-217125

(51) Int. Cl.
*G01N 33/22* (2006.01)
*G01N 33/00* (2006.01)
(Continued)

(52) U.S. Cl.
CPC ........ *G01N 33/225* (2013.01); *B60L 11/1838* (2013.01); *B60L 11/1898* (2013.01);
(Continued)

(58) Field of Classification Search
CPC .............. G01N 33/225; G01N 33/0031; B60L 11/1838; B60L 11/1898; G01L 13/00
See application file for complete search history.

(56) References Cited

U.S. PATENT DOCUMENTS

2012/0298256 A1* 11/2012 Mori .................... F17C 5/007
                                                          141/94
2013/0052553 A1*  2/2013 Inagi ................. H01M 8/04014
                                                         429/429
(Continued)

FOREIGN PATENT DOCUMENTS

JP          2007-26683          2/2007
JP          2010-3518           1/2010
(Continued)

*Primary Examiner* — Drew A Dunn
*Assistant Examiner* — Sailesh Thapa
(74) *Attorney, Agent, or Firm* — Finnegan, Henderson, Farabow, Garrett & Dunner LLP (57) ABSTRACT

This tank device comprises a fuel gas tank that stores fuel gas to be supplied to a gas consuming device, a first pressure sensor that detects the gas pressure when the fuel gas tank is filled with gas, a second pressure sensor that detects the pressure of the fuel gas supplied from the fuel gas tank to the gas consuming device, and a sensor output evaluation unit. The sensor output evaluation unit determines the gas pressure differential between the gas pressure detected by the first pressure sensor when the fuel gas tanks is filled with gas and the gas pressure detected by the second pressure sensor when the fuel gas is first supplied from the fuel gas tank to the gas consuming device after the gas filling, makes a judgment that there is not an output abnormality is any of the first and second pressure sensors if the gas pressure differential is within a given threshold value, and makes a judgement that there is an output abnormality in either of the first and second pressure sensors if the gas pressure differential is beyond the given threshold value.

18 Claims, 5 Drawing Sheets

(51) Int. Cl.
*G01L 13/00* (2006.01)
*B60L 11/18* (2006.01)
(52) U.S. Cl.
CPC .......... *G01L 13/00* (2013.01); *G01N 33/0031* (2013.01); *Y02T 90/34* (2013.01)

(56) References Cited

U.S. PATENT DOCUMENTS

2014/0182561 A1    7/2014  Ibizugbe, Jr.
2016/0079618 A1*   3/2016  Fukunaga .......... H01M 8/04089
                                                    429/429

FOREIGN PATENT DOCUMENTS

| JP | 2011-185357 A | | 9/2011 |
|----|---------------|---|--------|
| JP | 2012-058203 A | | 3/2012 |
| JP | 2012058203 | * | 3/2012 |
| JP | 2013-198295 A | | 9/2013 |
| JP | 20140187359 | * | 10/2014 |
| KR | 10-1998-0051113 A | | 9/1998 |

* cited by examiner

TANK DEVICE, A VEHICLE, AND A METHOD FOR EVALUATING AN OUTPUT OF A PRESSURE SENSOR

CROSS-REFERENCE TO RELATED APPLICATION

The present application claims priority from Japanese application P2014-217125 filed on Oct. 24, 2014, the content of which is hereby incorporated by reference into this application.

BACKGROUND

Field

The present invention relates to a tank device, a vehicle, and a method for evaluating an output of a pressure sensor.

Related Art

In supplying gas stored in a gas tank to a gas consuming device, the tank device detects the pressure of the supplied gas by a pressure sensor. As one example of each a gas consuming device, a fuel cell is cited. When fuel gas, or hydrogen gas, is supplied from the gas tank to the fuel cell, the gas pressure of the gas tank is reduced and adjusted to a given supply pressure by a pressure regulator such as a decompression valve. Then, a failure evaluation method is proposed whereby the gas pressure of the gas tank, which is on the primary side of the pressure regulator, and the gas supply pressure on the secondary side thereof are detected by individual pressure sensors during the time of supplying gas and if the pressure on the secondary side is higher than that on the primary side, an abnormality of sensor offset is detected (e.g. JP-2010-3518A).

SUMMARY

According to the method proposed in the patent literature referred to above, a failure of the pressure regulator and an output abnormality such as that of a pressure sensor that detects gas supply pressure on the secondary side is evaluated, but no output abnormality, or possibility thereof, of a pressure sensor that detects the gas pressure of the gas tank is detected. The pressure sensor that detects gas pressure has some deviations of detection characteristics due to its equipment configuration. These deviations or detection characteristics can differ depending on the pressure range detected by the sensor. This is because different ranges of detected pressure result in different equipment configurations of the sensor. Therefore, detection characteristics of the pressure sensor that detects the secondary-side gas supply pressure and those of the pressure sensor that detects the gas pressure of the gas tank often deviate from each otter as time goes by. Thus, once detection characteristics deviate, a detected value of the gas pressure of the gas tank is less than a detected value of the secondary-side gas supply pressure. Also, if the detected value of the pressure sensor on the gas tank side is deviated, reliability of failure evaluation and normality/abnormality evaluation of the sensor output is at risk. For that reason, an evaluation sorted capable of preventing deterioration of reliability in the sensor evaluation using the sensor output of the pressure sensor that detects the gas pressure of the gas tank has been called in.

In order to solve at least part of the problem described above, the present invention is implemented in the following aspects:

(1) According to one aspect of the present invention, a tank device is provided. This tank device comprises a fuel gas tank that stores fuel gas to be supplied to a gas consuming device, a first pressure sensor that detects gas pressure when the fuel gas is filled in the fuel gas tank, a second pressure sensor that detects the gas pressure of the fuel gas to be supplied to the gas consuming device from the fuel gas tank in the gas supply pipeline extending from the fuel gas tank to the gas consuming device, and a sensor output evaluation unit that determines the gas pressure differential between the gas pressure detected by the first pressure sensor when fuel gas tank is filled with gas and the gas pressure detected by the second pressure sensor when fuel gas is first supplied from the fuel gas tank to the gas consuming device after the gas filling, and makes a judgment of no output abnormality in any of the first and second pressure sensors if the gas pressure differential is within a given threshold value, and makes another judgment that there is an output abnormality in one of the first and second pressure sensors if the gas pressure differential is beyond the given threshold value.

The tank device of the above aspect detects the gas pressure of the fuel gas tank by the first pressure sensor when gas is filled in the fuel gas tank, and when fuel gas is first supplied from the fuel gas tank to the gas consuming device after the gas filling, detects the gas pressure of the fuel gas supplied from the fuel gas tank to the gas consuming device by the second pressure sensor in the gas supply pipeline extending from the fuel gas tank to the gas consuming device. Since gas is not consumed during the gas filling and the initial gas supply thereafter, the gas pressure in the fuel gas tank remains nearly the same. Also, the first and second pressure sensors are capable of detecting the filled gas pressure with nearly the same detection range, and the deviations of detection characteristics occur approximately to the same extent in both sensors. Therefore, in the output evaluation based on the gas pressure differential between the gas pressure detected by the first pressure sensor when the fuel tank is filled with gas and the gas pressure detected by the second pressure sensor when fuel gas is first supplied after the gas filling, the deviations of detection characteristics may possibly cancel each other. Then, the pressure of the fuel gas supplied from the fuel gas tank to the gas consuming device turns out equal to the gas pressure of the fuel gas tank during the gas supply. As a result, according to the tank device of the above aspect, deterioration of reliability is prevented in the output evaluation using the sensor output of the second pressure sensor that detects the pressure in fuel gas tank daring the gas supply. Meanwhile, since the tank device of the above aspect can also detect output abnormality in either of the first and second pressure sensors if the gas pressure differential between the gas pressure detected by the first pressure sensor when fuel gas tank is filled with gas and the gas pressure detected by the second pressure sensor when fuel gas is first supplied after the gas filling, deterioration of reliability in the evaluation of output abnormalities is prevented.

(2) In the tank device of the above aspect, the first pressure sensor may be made to detect the gas pressure of the fuel gas tank in a gas filling pipeline for filling gas in the fuel gas tank under a closed condition of the pipeline. This has the following advantage: If the tank device is provided with multiple fuel gas tanks, fuel gas is distributed via the gas filling pipeline to fill each fuel gas tank. Since the first pressure sensor detects the gas pressure of the fuel gas tank in the closed gas filling pipeline, there is no need for installing a pressure sensor in each fuel gas tank, which makes the device simpler.

(3) The tank device of any aspect described above may be made to have multiple fuel gas tanks, have a tank operation unit that operates to use the multiple fuel gas tanks, in sequence for supplying gas to the gas consuming device, store data on the gas pressure detected by the first pressure sensor when the fuel gas tank is filled with gas, determine the gas differential between the gas pressure detected by the second pressure sensor when the fuel gas is first supplied to the gas consuming device after the fuel gas is filled from the fuel gas tank that has been newly used for gas supply by the tank operation unit and the gas pressure detected by the first pressure sensor and stored in memory, and make a judgment of no output abnormality in any of the first and second pressure sensors if the gas pressure differential is within a given threshold value. This has the following advantage: In case of using multiple fuel gas tanks in sequence for supplying gas to the gas consuming device, the fuel gas tank that has been newly used for gas supply maintains the gas filling pressure after the gas filling so that it supplies fuel gas to the gas consuming device under the gas filling pressure. Therefore, according to the tank device of this aspect, the output evaluation using the gas pressure detected by the second pressure sensor is carried out as many times as the number of fuel tanks after the gas filling, thus more effectively preventing deterioration of reliability in the output evaluation using the output of the second pressure sensor.

(4) The tank device of any aspect described above may be made not to detect any output abnormality using the detected gas pressure under a situation where the charging voltage of the battery that charges the first and second pressure sensors with a driving voltage is lowered, or, may be made to clear the judgment of an output abnormality made by using the detected gas pressure. This has the following advantage: Under a situation where the charging voltage of the battery is lowered, reliability of the gas pressure, not only the one detected by the first pressure sensor but also the one detected by the second pressure sensor is reduced. Therefore, the tank device of this aspect can avoid making any judgment of low reliability by not carrying out any evaluation on the output abnormality rising the detected gas pressure. Also, by means of clearing the judgment of an output abnormality made by using the detected gas pressure, any judgment of low reliability is prevented from being provided.

(5) In the tank device of any aspect described above, the gas consuming device is a fuel cell. This way, the above effect is achieved in supplying fuel gas from the fuel gas tank to the fuel cell.

(6) According to another aspect of the present invention, a vehicle with a fuel cell mounted on board is provided. This vehicle has a tank of any aspect described above that supplies fuel gas to the fuel cell as a gas consuming device. Therefore, according to the vehicle of this aspect, deterioration of reliability is prevented in the output evaluation using the sensor output of the second pressure sensor that detects the fuel gas pressure during the gas supply.

(7) According to still another aspect of the present invention, a method for evaluating an output of a pressure sensor is provided. The output evaluation method for this pressure sensor is a method for evaluating an output of the pressure sensor used to detect the pressure or the fuel gas tank that stores fuel gas to be supplied to the gas consuming device, which comprises a process of detecting the gas pressure of the fuel gas tank by the first pressure sensor when the fuel gas tank is filled with gas to obtain the filled fuel gas pressure of the fuel gas tank, a process of detecting the gas pressure of the fuel gas tank by the second pressure sensor in the gas supply pipeline that extends from the fuel gas tank to the gas consuming device when the fuel gas is first supplied from the fuel gas tank to the gas consuming device after the gas filling to obtain the fuel gas pressure of the fuel gas tank at the earliest supply, and a process of determining the gas pressure differential between the filled fuel gas pressure obtained and the fuel gas pressure at the earliest supply to make a judgment of no output abnormality in any of the first and second pressure sensors if such gas pressure differential is within a given threshold value.

According to the method for evaluating an output of the pressure sensor of the above aspect, deterioration of reliability is prevented in the output evaluation using the sensor output of the second pressure sensor that detects the gas pressure of the fuel gas tank during the gas supply. Also, according to the output evaluation method of this aspect, there is a judgment that there is an output abnormality in either of the first and second pressure sensors if the pressure differential between the gas pressure detected by the first pressure sensor during the gas supply to the fuel gas tank and the gas pressure detected by the second pressure sensor during the initial gas supply after the gas filling is beyond the given threshold value, and deterioration of reliability regarding this judgment on the output abnormality can also be prevented.

The present invention is implemented in various aspects and is applied, for example, as a fuel gas supply device that supplies fuel gas to a gas consuming device, a fuel gas supply method, a fuel cell system or a power generation system that obtains electric power by supplying fuel gas to the fuel cell from the fuel gas tank.

BRIEF DESCRIPTION OF THE DRAWINGS

The present disclosure is illustrated by way of example and not by way of limitation in the figures of the accompanying drawings, in which the like reference numerals indicate like elements and in which.

DESCRIPTION OF THE EMBODIMENTS

Figure 1:
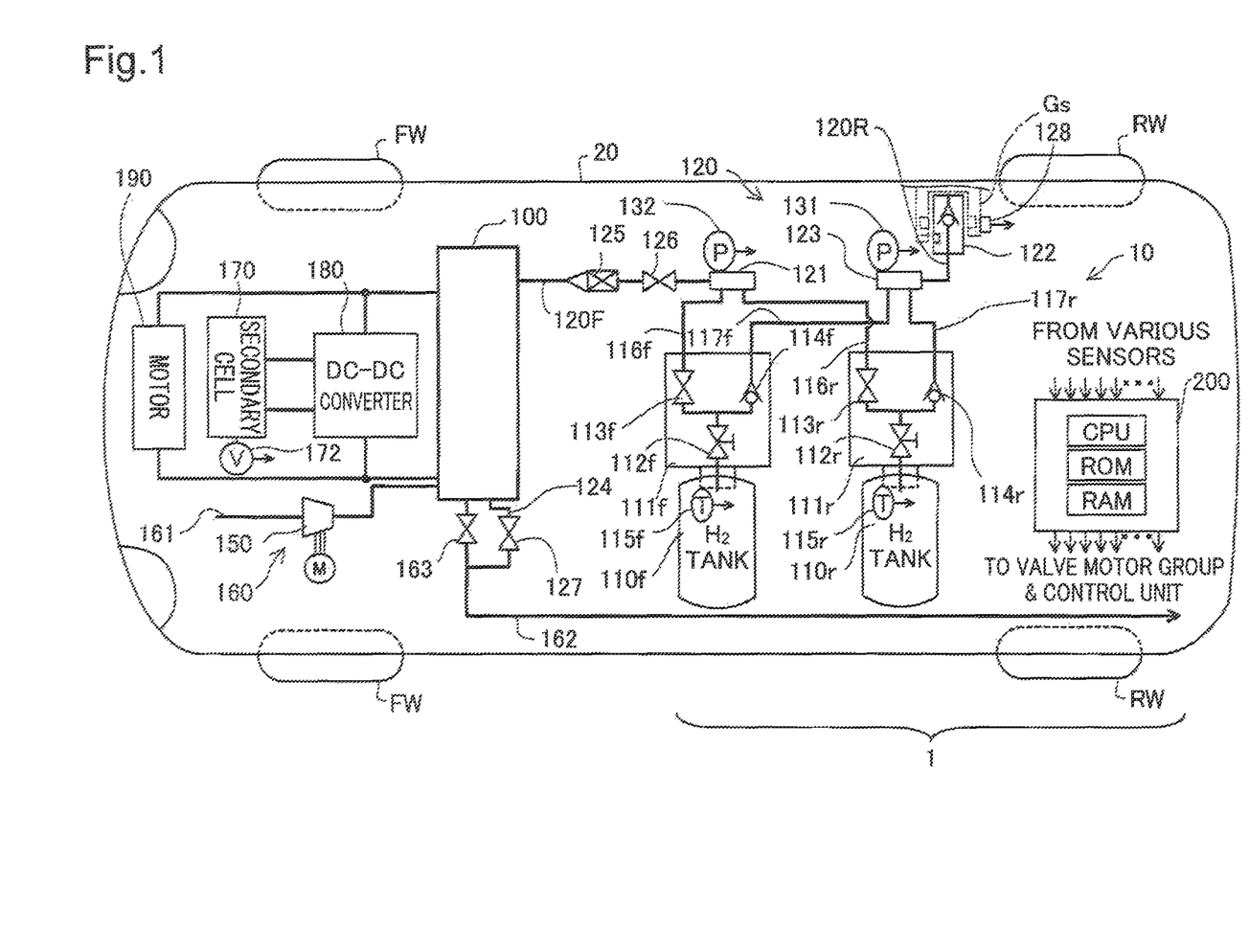
FIG. 1 is an illustrative diagram schematically showing a fuel cell system 10 as a first embodiment of the present invention.

Embodiments of the present invention are described below in reference to the drawings. FIG. 1 is an illustrative diagram schematically showing a fuel cell system 10 equipped with a tank device 1 as a first embodiment of the present invention.

As shown in the drawing, this tank device 1 is built in the fuel cell system 10 as part thereof. The fuel cell system 10 is mounted on a fuel cell vehicle 20 and comprises a fuel cell 100, a hydrogen gas supply system 120 including two gas tanks, an air supply system 160 including a motorized compressor 150, a cooling system, not shown, a secondary cell 170, a DC-DC converter 130, and a control unit 200. The fuel cell 100 is configured by layering multiple power generation modules equipped with a membrane electrode assembly (MEA), not shown, the MEA is combined with electrodes of an anode and a cathode on both sides of the electrolyte membrane and is installed under the vehicle floor between the forward wheels FW and rear wheels RW. The fuel cell 100 generates power by electrically reacting hydrogen contained in the hydrogen gas supplied from the hydrogen gas supply system 120 described later and oxygen contained in the air supplied from the air supply system 160, thus driving the loads such as a driving motor 190 for the front and rear wheels using the generated power.

The hydrogen gas supply system 120 comprises two hydrogen gas tanks 110*f*, 110*r* that store high pressure hydrogen gas as fuel gas to be supplied to the fuel cell 100, a fuel gas supply pipeline 120F reaching the fuel cell 100, a supply-side manifold 121 at the end of the gas flow path, a hydrogen filling pipeline 120R extending frost a receptacle 122 to a filling-side manifold 123, and a discharge pipeline 124 that discharges unconsumed hydrogen gas (anode off-gas) to the atmosphere. Other than these, the hydrogen gas supply system 120 includes a first gas pressure sensor 131 provided in the hydrogen filling pipeline 120R, an injector 125 provided in the fuel gas supply pipeline 120F, a decompression valve 126, a second gas pressure sensor 132, and also a discharge flow control valve 127 provided in the discharge pipeline 124. The supply of hydrogen gas to the fuel cell 100 by the hydrogen gas supply system 120 is performed by using the hydrogen gas tanks 110*f*, 110*r* as sources of supply via the second gas pressure sensor 132, decompression valve 126 and injector 125. The decompression vale 126 operates upon receipt of signals from the control unit 200 as described later, and supplies post-decompression hydrogen gas to the injector 125. The injector 125 operates upon receipt of signals from the control unit 200 as described later, and supplies hydrogen gas jet to the fuel cell 100 after controlling the flow of hydrogen gas. The second gas pressure sensor 132 is provided in supply-side tank pipelines 116*f*, 116*r* that converge at the supply-side manifold 121 on the immediate downstream side of the convergence. Therefore, the second gas pressure sensor 132 detects the pressure on the upstream side of the decompression valve 126 in the fuel gas supply pipeline 120F, that is, the pressure of hydrogen gas supplied to the fuel cell 100 from the hydrogen gas tanks 110*f*, 110*r*. The handling of data on the hydrogen gas pressure detected by the first and second gas pressure sensors 131, 132 are described later in detail.

The hydrogen gas tanks 110*f* and 110*r* are resin-made tanks with a fiber-reinforced layer made by winding a fiber around the outer periphery of a resin-made liner. The hydrogen gas tanks 110*f* and 110*r* are mounted on the fuel cell vehicle 20 to be laid out in the vehicular lateral direction in a layout where the hydrogen gas tank 110*f* comes in front of the hydrogen gas tank 110*r* in the vehicular longitudinal direction. These hydrogen gas tanks 110*f*, 110*r* are supplied and filled with high-pressure hydrogen gas at a hydrogen gas station, not shown, and each stores a given amount of hydrogen gas. Also, the hydrogen, gas tanks 110*f*, 110*r* are provided with mouthpieces 111*f*, 111*r*, respectively, which are provided with main valves 112*f*, 112*r*, on-off valves 113*f*, 113*r*, check valves 114*f*, 114*r*, and temperature sensors 115*f*, 115*r* that detect temperature in each tank, respectively. One connection side of the main valves 112*f*, 112*r* is connected to the hydrogen gee tank 110*f* and 110*r*, respectively, and the otter connection side of the main valves 112*f*, 112*r* is each forked to connect to the on-off valves 113*f*, 113*r* as well as check valves 114*f*, 114*r*, respectively. The check valves 114*f*, 114*r* are each connected to the filling-side manifold 123 at filling-side tank pipelines 117*f*, 117*r*, respectively, to control the gas to pass only from the filling-side manifold 123 toward the hydrogen gas tanks 110*f*, 110*r*.

The main valves 112*f*, 112*r* are usually operated manually in the direction of opening the flow path to keep the flow path open for supplying and discharging hydrogen gas to and from the hydrogen gas tanks 110*f*, 110*r*. The on-off valves 113*f*, 113*r* open or close under the control of the control unit 200, described later, and are connected to a supply-side manifold 121 in the supply-side tank pipelines 116*f*, 116*r*. In such a pipeline configuration, the hydrogen gas tanks 110*f*, 110*r* are connected to the fuel cell 100 via the supply-side tank pipelines 116*f*, 116*r* that fork out of the supply-side manifold 121 of the fuel gas supply pipeline 120F and connect in parallel to the fuel cell 100. In this case, each of these tank pipelines on the supply side and filling side is made attachable and detachable on the side of the supply-side manifold 121, filling-side manifold 123 or the tank mouthpieces 111*f*, 111*r* at the time of replacing the tank. The temperature sensors 111*f*, 115*r* are provided with a connector attachable and detachable at the time of replacing the tank, and after the installation, are connected to the control unit as described later, by a connector and a signal line, not shown, so as to output the detected tank temperature to the control unit 200. The on-off valves 113*f*, 113*r* are also connected to the control unit 200, described later, by a connector and a signal line, not shown, to perform open-shut operations under the control of the control unit 200.

The hydrogen gas supply system 120 provided with the pipeline configuration described above supplies hydrogen gas from one of the hydrogen gas tanks 110*f*, 110*r* selected as a supply tank or from both of them to the fuel cell 100 under the control of the control unit 200, described later. The control unit 200 controls the flow rate at the injector 125 and decompression (pressure adjustment) at the decompression valve 126 and supplies hydrogen gas to the anode of the fuel cell 100. Meanwhile, the anode off-gas used for power generation in the fuel cell 100 is controlled its flow rate by the discharge flow control valve 127 in the discharge pipeline 124 to be discharged to the atmosphere via a discharge pipeline 162, described later. The injector 123 is adjustable from sere gas flow, and if the flow is set to zero, the fuel gas supply pipeline 120F is in a closed state. In the present embodiment, the amount of hydrogen gas supplied to the fuel cell 100 is controlled by this injector 125, but the injector 125 may be used only for supplying hydrogen gas jet by providing a flow control valve that controls the amount of hydrogen gas supplied to the fuel cell 100 on the upstream side of the injector 125.

The receptacle 122 of the hydrogen gas supply system 120 is located at a gas filling inlet that is equivalent to the fuel filling opening on the side or rear of the conventional gasoline-powered vehicle and is covered by the exterior thereof. The receptacle 122 is provided with a nozzle sensor 128 that detects installation of a gas filling nozzle Gs. In the process of filling hydrogen gas at a hydrogen gas station, not shown, the receptacle 122 is installed with the gas filling nozzle Gs and hydrogen gas supplied at high pressure is introduced to the filling-side manifold 123. The supplied high pressure hydrogen gas is introduced to the hydrogen gas tanks 110*f*, 110*r* to be filled therein via the filling side pipelines 117*f*, 117*r* and the check valves 114*f*, 114*r*. In the process of such gas filling, the temperature sensors 115*f*, 115*r* provided in the hydrogen gas tanks 110*f*, 110*r*, respectively, output a signal reflecting the temperature in each tank to the control unit 200 and an in-station control unit. The signal reflecting temperature in each tank is used for checking and detecting the amount of filled gas and the filling pressure. Also, the condition of connection between the receptacle 122 and the gas filling nozzle Gs is detected by the nozzle sensor 128, and the control unit 200 that receives the detected signals makes a judgment on the status of filling such as "gas filling in progress" or "gas filling complete" based on the signals.

The first gas pressure sensor 131 for detecting the pressure of the hydrogen gas supply system 120 is provided in the filling-side manifold 123. This first gas pressure sensor 131 detects the pressure of hydrogen gas passing through the filling-side tank pipelines 117f, 117r that fork out of the filling-side manifold 123 at each tank, that is, the filled gas pressure of the hydrogen gas tanks 110f, 110r. Since the hydrogen filling pipeline 120R is closed by the receptacle 122 and check valves 114f, 114r after the completion of hydrogen gas filling, the first gas pressure sensor 131 ends up detecting the gas pressure at the completion of gas filling in the hydrogen gas tanks 110f, 110r.

Next, the air supply system 160 that supplies oxygen to the cathode of the fuel cell 100 is described. The air supply system 160 comprises an oxygen supply pipeline 161 that reaches the cathode of the fuel cell 100 via the compressor 150, the discharge pipeline 162 that discharges unconsumed air (cathode off-gas) to the atmosphere, and a discharge flow control valve 163 in the pipeline. The air supply system 160 includes a supply path whereby the air taken in from the open end of the oxygen supply pipeline 161 is supplied to the cathode of the fuel cell 100 after flow adjustment at the compressor 150 and a discharge route whereby the cathode off-gas is discharged to the atmosphere via the discharge pipeline 162 at a flow rate adjusted by the discharge flow control valve 163 in the discharge pipeline 162. The fuel cell system 10 is provided not only with the supply system described above but with a cooling system, not shown, that cools the fuel cell 100 by a circulated supply of cooling medium, which is not directly related to the subject matter of the present invention, and therefore the description thereof is omitted.

The secondary cell 170 is connected to the fuel cell 100 via the DC-DC converter 180 and functions as a power source different from the fuel cell 100. The secondary cell 170 not only supplies charged power to the driving motor 190 in a shutdown state of the fuel cell 100 but also supplies power to various sensors such as a first gas pressure sensor 131 and second gas pressure sensor 132 via a back converter, not shown. As the secondary cell 170, a lead rechargeable battery, a nickel-metal hydride battery or a lithium-ion battery, for example, may be adopted. The secondary cell 170 is connected to a capacity detection sensor 172. The capacity detection sensor 172 detects the state of charge (SOC) of the secondary cell 170 and outputs the detected SOC to the control unit 200.

The DC-DC converter 180 has a function of controlling the charging and discharging of the secondary cell 170 upon receipt of control signals from the control unit 200 and adjusting the voltage level applied to the driving motor 190.

The control unit 200 is composed of so-called a microcomputer equipped with CPU, ROM, RAM and so forth that perform logical operations. The control unit 200 is in charge of various controls over the injector 125 and fuel cell 100 including the open-shut controls of the above various valves upon receipt of signals from various sensors that detect the vehicle's driving status including the accelerator position sensor installed at the accelerator and signals from other sensors such as the first gas pressure sensor 131 and temperature sensors 115f, 115r that detect the status of the hydrogen gas supply system 120. In addition to the configuration in the control unit 200 that performs the output evaluation of the pressure sensor, described later, the hydrogen tanks 110f, 110r, first gas pressure sensor 131 and second gas pressure sensor 132 are composing the tank device 1. The first and second gas pressure sensors 131, 132 belong to the subordinate concept of the first and second pressure sensors, and within the control unit 200, the configuration that performs the output evaluation of the pressure sensor, described later, belongs to the subordinate concept of the output evaluation unit.

Figure 2:
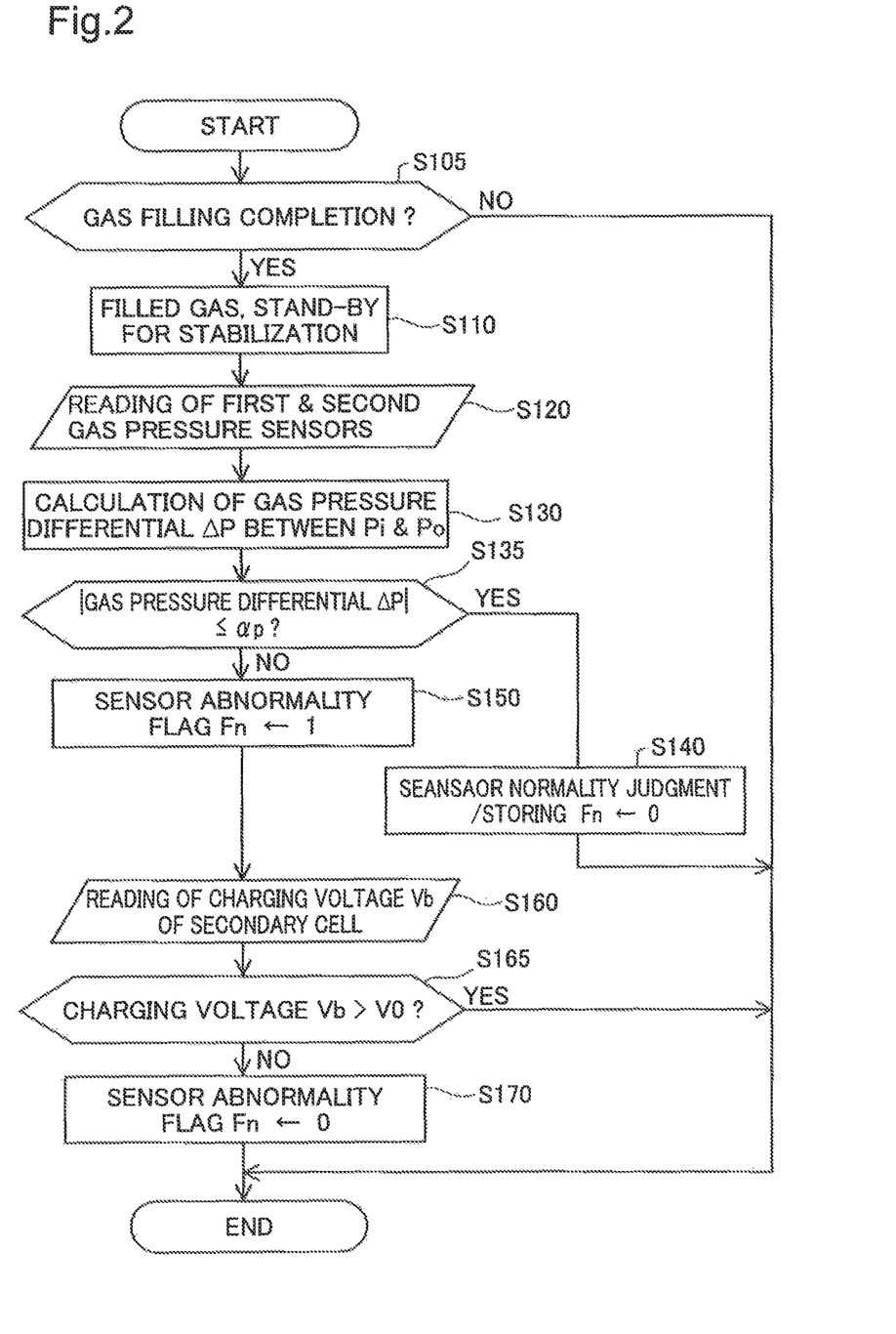
FIG. 2 is a flow chart showing an output evaluation process of a pressure sensor.

Next, the output evaluation process of the pressure sensor performed in the tank device 1 in the fuel cell system 10 of the present embodiment is described below. FIG. 2 is a flow chart showing an output evaluation process of the pressure sensor. In the following descriptions, the hydrogen gas tanks 110f and 110r are collectively called, the hydrogen gas tank 110 for the convenience sake, and if needed to be called separately for each tank in relation to FIG. 1, these tanks are distinguished between the hydrogen gas tank 110f and hydrogen gas tank 110r.

The output evaluation process of the pressure sensor shown in FIG. 2 is a process repeated by the control unit 200 at given intervals from the start of gas filling. The start of gas filling means the time when an ignition switch, not shown, of the fuel cell vehicle 20 is turned off and a gas filling nozzle Gs is attached to the receptacle 122. Once this process is started, the control unit 200 makes a judgment whether the gas filling is complete or not (Step S105). If a negative judgment is made, the present routine is ended for now without any further process on the assumption that the conditions for making a judgment on the completion of gas filling are not yet met. The evaluation judgment on the completion of gas filling is made based on the signal or the like detected by the nozzle sensor 128 that detects the connection between the receptacle 122 and the gas filling nozzle Gs. In Step S105, a negative judgment is made during the filling of hydrogen gas or after the vehicle's start of running.

Once the gas filling nozzle Gs is removed from the receptacle 122 following the positive judgment on the completion of gas filling made in Step S105, that is, once the gas filling using the gas filling nozzle Gs is complete, the control unit 200 stands by until the conditions of gas filled in the hydrogen gas tank 110 stabilizes (Step S110). In the gas filling process, the gas pressure rises in the initial filling stage and stabilizes as the filling of the tank continues to bring the gas pressure or the tank to a certain level such as 70 Mpa. Meanwhile, if any "ON" operation of the ignition switch is performed after the filling of hydrogen gas, a starting check of the fuel cell 100 such as opening of the on-off valves 113f, 113r is performed. The gas pressure fluctuates also during this short period of time. In Step S110, the system waits for such gas stabilization. In response to the "ON' operation of the ignition switch, the control unit 200 performs a fuel cell operation control, not shown, and opens both the on-off valves 113f, 113r of each hydrogen gas tank 110 so as to keep the fuel cell 100 under idling. Therefore, after the stand-by period for gas stabilization in Step S110, hydrogen gas in the tank is supplied from the hydrogen gas tank 110 to the fuel cell 100 by the control unit 200. The hydrogen gas pressure at the initial gas supply after the gas filling is sensed by the second gas pressure sensor 132 and obtained as the initial gas supply pressure P0. Also, the pressure of hydrogen gas in the tank at the completion of filling is sensed by the first gas pressure sensor 131 and obtained as the gas filling pressure Pi. Detection of gas pressure by the first and second gas pressure sensors 131, 132 may be performed with the injector 125 and the on-off valves 113f, 113r all open.

Following the stand-by period for gas stabilization, the control unit 200 reads the gas pressure detected by two pressure sensors, that is, the first and second gas pressure sensors 131, 132 (Step S120), and calculates the gas pressure differential ΔP between the filled gas pressure Pi detected by the first gas pressure sensor 131 and the initial gas supply pressure Po detected by the second gas pressure sensor 132 (Step S130). Thereafter, the control unit 200 compares an absolute value of the calculated gas pressure differential ΔP with a predetermined threshold value αp to judge whether or not the absolute value of the gas pressure differential ΔP is equal or less than the threshold value αp (Step S135). In the present embodiment, this threshold value αp was defined as follows:

Once the gas is stabilized after the gas filling, the pressure of the hydrogen gas tank 110 at the completion of filling (the filled gas pressure Pi), which is the gas pressure detected by the first gas pressure sensor 131 turns out to be near equal to the initial gas supply pressure Po of the gas sent to the fuel cell 100 after the gas filling, which is the gas pressured detected by the second gas pressure sensor 132. Therefore, unless there is any sensing abnormality in either of the above sensors, the filled gas pressure Pi detected by the first gas pressure sensor 131 becomes equal to the initial gas supply pressure Po detected by the second gas pressure sensor 132. Even if these sensors have characteristic deviations such as temporal drifting or the like, they have the same detection range so that it is assumed that their deviations of detection characteristics are to the same extent. In the fuel cell system 10 of the present embodiment, the threshold value αp was defined in consideration of the detection range of these sensors and the extent of deviation of detection characteristics allowed for each of them in sensing gas pressure.

In Step S135 described above, once a positive judgment is made that the absolute value of the gas pressure differential ΔP is equal or less than the threshold value αp, the control unit 200 makes a judgment that the output of any of the first gas pressure sensor 131 and second gas pressure sensor 132 is normal without any abnormality and stores the positive judgment data in a given memory area while resetting the value of the sensor abnormality flag Fn, described later, to zero (Step S140). Thus, storing data indicating normal operation of the pressure sensor is beneficial in referencing the history of sensor operations and taking countermeasures during periodical inspections and the like. If the pressure sensor is normal, the control unit 200 resets the value of the sensor abnormality flag Fn in Step S140 and ends the present routine for now. Therefore, the sensor abnormality flag Fn keeps the reset status thereafter until the sensor abnormality flag Fn is set in Step S150 as described later.

Now, since the gas pressure read in Step S130 is the initial gas supply pressure after the completion of gas filling, the filled gas pressure Pi detected by the first gas pressure sensor 131 and the initial gas supply pressure Po detected by the second gas supply pressure 132 are both equivalent to a given filled gas pressure (e.g. 70 Mpa). Or, they are deviated from this filled gas pressure to fall within the allowable deviation range of detection characteristics. Therefore, assuming that either of the filled gas pressure Pi and the initial gas supply pressure Po is deviated from the given filled gas pressure beyond the allowable deviation range of detection characteristics, the system may be made to make a judgment that there is an output abnormality in the pressure sensor that detected the deviated gas pressure. Such a judgment may easily be made by receiving the value of the filled gas pressure from the hydrogen gas station, for example. Also, even when the gas pressure differential ΔP is equal or less than the threshold, value αp, the system may be made to make a judgment that each of the first gas pressure sensor 131 and second gas pressure sensor 132 has an output abnormality if the filled gas pressure Pi and the initial gas supply pressure Po are both deviated from the given filled gas pressure beyond the allowable deviation range of detection characteristics.

In Step S135 described above, once a negative judgment is made that the absolute value of the gas pressure differential ΔP is not equal or less than the threshold value αp, the control unit 200 sets a value of 1 for the sensor abnormality flag Fn that indicates an output abnormality in either of the first gas pressure sensor 131 and second gas pressure sensor 132 (Step S150). In response to this setting of the sensor abnormality flag Fn, the control unit 200 performs lighting control of the abnormality warning lamp in the vehicular cabin in the process of auxiliary machinery control routine, not shown, while storing the data indicating an output abnormality in either of the first gas pressure sensor 131 and second gas pressure sensor 132 in a given memory area. This storing of data on the output abnormality is also beneficial in referencing the history of sensor operations and taking countermeasures during periodical inspections and the like.

Following Step S150, the control unit 200 reads the charging voltage Vb of the second fuel 170 using the capacity detection censor 172 (see FIG. 1) (Step S160) and compares the reading of the charging voltage with a given threshold value V0 (Step S165). In the present embodiment, this threshold value V0 was defined as follows:

Being charged with a driving voltage by the second cell 170, the first gas pressure sensor 131 and second gas pressure sensor 132 detect the gas pressure, more specifically, the hydrogen gas pressure in the hydrogen gas tank 110 as described above in the hydrogen filling pipeline 120R or fuel gas supply pipeline 120F. Assuming that the voltage charged to each sensor falls short of a prescribed driving voltage, reliability of the gas pressure detection gets deteriorated even if the first gas pressure sensor 131 and second gas pressure sensor 132 are capable of performing normal detection. Therefore, in the fuel cell system 10 of the present embodiment, the lower limit of driving voltage that can perform normal detection was defined in advance by means such as experiments, and this lower limit of defined driving voltage was assumed to be the threshold value V0.

Having made a positive judgment that the charging voltage Vb exceeds the given threshold V0 in the process of comparison in Step S165, the control unit 200 ends the present routine for now without further process, because the gas pressure detected by either the first gee pressure sensor 131 or second gas pressure sensor 131 does not take on any value derived from a low driving voltage. Therefore, the sensor abnormality flag Fn maintains a set condition. Since the fuel cell system 10 of the present embodiment uses the secondary cell 170 as a source of driving voltage, there is a possibility that the voltage that is outputted to the sensor or else be limited depending on the status of power output to the driving motor 100 even with some margin left for the voltage Vb. Therefore, the system may be made to make a judgment whether or not the defined driving voltage is charged to the sensor or else depending on the charging voltage Vb in the Step 165, considering the status of power output to the driving motor 190.

Once having made a negative judgment that the charging voltage Vb is no more than the given threshold value V0 in the comparison in Step S165, the control unit 200 resets the value of the sensor abnormality flag Fn to zero (Step S170) by determining that the output abnormality is not necessarily caused by abnormality of the sensor itself because the gas pressures detected by either the first gas pressure sensor 131 or second gas pressure sensor 132 takes on a value derived from a low driving voltage, and terminates the present routine. Therefore, the sensor abnormality flag Fn keeps the reset status thereafter until the sensor abnormality flag Fn is set in Step S150 described above.

As described above, the tank device 1 in the fuel cell system 10 of the present embodiment defects the filled gas pressure Pi of the hydrogen gas tank 110 using the first gas pressure sensor 131 in the hydrogen filling pipeline 120R when the hydrogen gas tank 110 is filled with hydrogen gas, and when hydrogen gas is first supplied from the hydrogen gas tank 110 to the fuel cell 100 after the gas filling, it detects the initial gas supply pressure Po of the hydrogen gas tank 110 during that time using the second gas pressure sensor 132 in the fuel gas supply pipeline 120F. Then, if the absolute value of the gas pressure differential $\Delta P$ between the filled gas pressure Pi and the initial gas supply pressure Po is equal or less than the threshold value $\alpha p$ (positive judgment in Step (S135), a judgment, is made that the output of any of the first gas pressure sensor 131 and second gas pressure sensor 132 is normal without any abnormality (step S140). The judgment on the output as "normal" using the sensor output of the second gas pressure sensor 132 that detects the gas pressure of the hydrogen gas tank 110 when hydrogen gas is supplied to the fuel cell 100 is ensured of its reliability as described below.

After the filling of hydrogen gas and at the initial gas supply thereafter, both the first gas pressure sensor 131 and second gas pressure sensor 132 target for the same hydrogen gas filled in the hydrogen gas tank 110 as a detection object as described above. Therefore, the filled gas pressure Pi obtained from the first gas pressure sensor 131 and the initial gas supply pressure Po obtained from the second gas pressure sensor 132 are each equivalent to a given filled gas pressure (e.g. 70 Mpa) as described above. Or, they deviate from the filled gas pressure to fall within the allowable deviation range of defection, characteristics. Then, the first gas pressure sensor 131 and second gas pressure sensor 132 have nearly the same detection range and the deviations of detection characteristics occur approximately to the same extent, although the occurrence timing of such deviations is different from each other. Therefore, in the process of output evaluation of the pressure sensor based on the gas pressure differential $\Delta P$ between the filled gas pressure Pi when gas filling is complete and the initial gas supply pressure Po at the initial gas supply after the gas filling, the deviation of detection characteristics is considered small. As a result, according to the fuel cell system 10 of the present embodiment, the output evaluation (judgment as normal) using the sensor output of the second gas pressure sensor 132 that detects the gas pressure of the hydrogen gas tank 110 when hydrogen gas is supplied to the fuel cell 100 is ensured of its reliability.

The tank device 1 of the fuel cell system 10 of the present embodiment makes a judgment that there is an output abnormality in either of the first gas pressure sensor 131 and second gas pressure sensor 132 (Step S150) if the absolute value of the gas pressure differential $\Delta P$ between the filled gas pressure Pi and the initial gas supply pressure Po is novo equal or less than a threshold value $\alpha p$ (negative judgment in Step S135). Even in the output evaluation finding an output abnormality using the sensor output of the second gas pressure sensor 132 that detects the gas pressure of the hydrogen gas tank 110 when hydrogen gas is supplied to the fuel cell 100, its reliability is ensured as described above. Then, according to the fuel cell system 10 of the present embodiment, by means of informing the output abnormality in either of the first gas pressure sensor 131 and the second gas pressure sensor 132 by a warning lamp or else via the set of the sensor abnormality flag Fn and this flag set, restoration of the sensor output such as replacing the sensor is prompted.

The tank device 1 of the fuel cell system 10 of the present embodiment detects the filled gas pressure Pi of the two hydrogen gas tanks 110f, 110r solely by the first gas pressure sensor 131 in the hydrogen filling pipeline 120R in a closed state thereof. Therefore, according to the fuel cell system 10 of the present embodiment, there is no need for installing the first gas pressure sensor 131 individually in the hydrogen gas tasks 110f, 110r, thus enabling to simplify the configuration [of the tank] and reduce the cost thereof.

If the driving voltage for the first gas pressure sensor 131 or the second gas pressure sensor 132 is lower than a prescribed voltage, reliability of the detected gas pressure, not only for the first pressure sensor 131 but also for the second pressure sensor 132 is reduced. Based on these premises, the fuel cell system 10 of the present embodiment resets the value of the sensor abnormality flag Fn to zero (Step S170) by determining that the output abnormality is not necessarily caused by abnormality of the sensor itself if the charging voltage Vb of the secondary cell 170 that charges the first gas pressure sensor 131 and second gas pressure sensor 132 with the driving voltage is no more than the given threshold value V0 (negative judgment in Step S165) because the gas pressure detected by either of these sensors takes on a value derived from a low driving voltage, and then clears the judgment in the output evaluation finding an output abnormality using the sensor output of the second gas pressure sensor 132. Therefore, according to the fuel cell system 10 of the present embodiment, providing output evaluation with low reliability and informing abnormality by a warning lamp and the like based on an output evaluation with low reliability is avoided.

Since the fuel cell vehicle 20 of the present embodiment has a fuel cell system 10 mounted on board that is equipped with the tank device 1 described above, it can prevent deterioration of reliability in the output evaluation during running of the vehicle after the gas filling, using the output sensor of the second gas pressure sensor 132 that detects the gas pressure of the hydrogen gas tank 110 during the gas supply.

Figure 3:
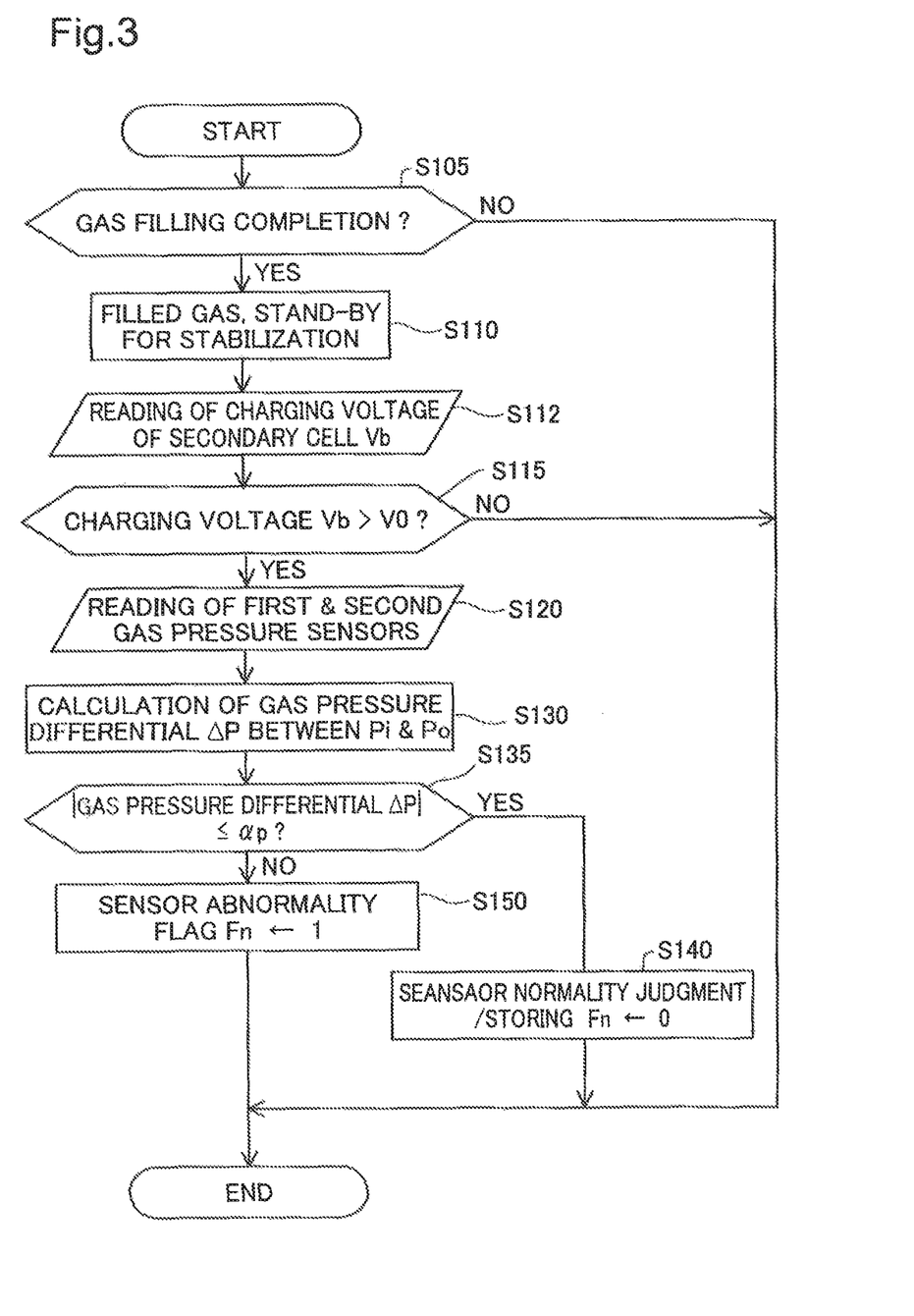
FIG. 3 is a flow chart showing an output evaluation process of the pressure sensor according to the second embodiment.

Next, another embodiment is described. FIG. 3 is a flow chart showing an output evaluation process of the pressure sensor according to the second embodiment. In the output evaluation process of the second embodiment, Steps S105 to 110 are carried out as has been done in the first embodiment described above, and once the gas is stabilized after filling the tank, the control unit 200 reads the charging voltage Vb of the secondary cell 170 from the capacity detection sensor 172 (see FIG. 1) (Step S112), and compares the reading of charging voltage Vb with then given threshold value V0 mentioned above (Step S115). Then, once the control unit 200 makes a negative judgment that the charging voltage Vb is no more than the given threshold value V0 in the comparison in Step S115, it ends the present routine for now without further process.

Meanwhile, once a positive judgment is made that the charging voltage Vb exceeds the given threshold value V0 in the comparison in Step S115, the following steps are taken in succession, assuming no output abnormality derived from a low driving voltage: Reading of gas pressures detected by the first gas pressure sensor 131 and second gas pressure sensor 132 (Step S120), calculation of the gas pressure differential ΔP between the readings of the filled gas pressure Pi and initial gas supply pressure Po (Step S130), and comparing the absolute value of the gas pressure differential ΔP with the threshold value αp. Then, following the positive judgment in Step S135, the control unit 200 makes a judgment that the output of any of the first gas pressure sensor 131 and second gas pressure sensor 132 is normal without any abnormality, stores the positive judgment data in a given memory area while resetting the value of the sensor abnormality flag Fn to zero (Step S140), and ends the present routine for now.

If a negative judgment is made that the absolute value of the gas pressure differential ΔP is not equal or less than the threshold value αp in Step S135, the control unit 200 sets the value 1 for the sensor abnormality flag Fn that indicates an output abnormality in either of the first gas pressure sensor 131 and second gas pressure sensor 132 (Step S150) and ends the present routine for now. Since the sensor abnormality flag Fn set in Step S150 is reset upon replacement of the sensor, informing of abnormality following the sensor abnormality flag Fn continues until the sensor is replaced. Thus, the sensor replacement is prompted more effectively.

The fuel cell system 10 of the second embodiment described above does not make any judgment on the output itself using the sensor output of the second gas pressure sensor 132 that detects the gas pressure of the hydrogen gas tank during the gas supply due to impossibility of ensuring reliability for the output of the pressure sensor. Therefore, the fuel cell system 10 of the present embodiment is made not to provide an output evaluation with lower reliability. Instead, the fuel cell system 10 of the present embodiment carries out an output evaluation using the sensor output of the second gas pressure sensor 132 that detects the was pressure of the hydrogen gas tank 110 during the gas supply under a situation where there is no output abnormality derived from a low driving voltage, thus enabling to avoid deterioration of reliability in the output evaluation.

Figure 4:
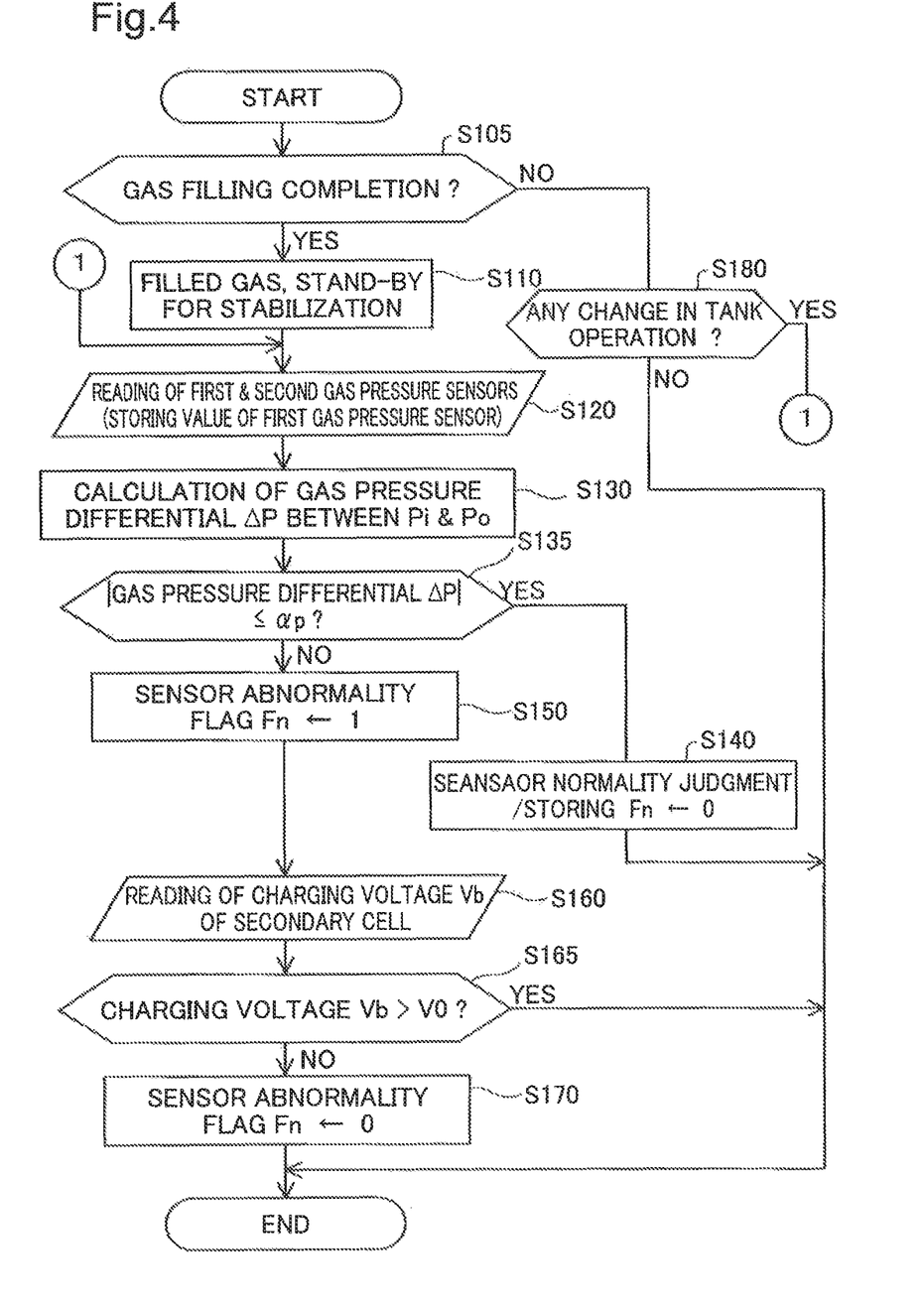
FIG. 4 is a flow chart showing an output evaluation process of the pressure sensor according to the third embodiment.

FIG. 4 is a flow chart showing an output evaluation process of the pressure sensor according to the third embodiment. The present embodiment is characterized by the sequential use of the hydrogen gas tanks 110f and 110r for supplying gas to the fuel cell 100. For the convenience of description, it is assumed that the gas filling is performed for the hydrogen gas tanks 110f and 110r at the same time, and after the gas filling, the hydrogen gas tank 110f is primarily used for gas supply to the fuel cell 100. Subsequently, when the amount of gas in the hydrogen gas tank 110f drops down to a half level, for example, as the vehicle continues to run, the gas is supplied to the fuel cell 100 from the hydrogen gas tank 110r in lieu of the hydrogen gas tank 110f, and thereafter the gas supply is provided from both of the gas tanks.

As shown in the output evaluation process of the present embodiment in FIG. 4, a judgment is made whether the gas filling is complete or not (Step S105) as has been done in the previous embodiments described above, and if a negative judgment is made, another judgment is made whether there is any change or not in the operation of the tank described above (Step S180). Here, if a judgment is made that there was no operational change, the control unit 200 ends the present routine for now without further process. If a positive judgment is made that there was an operational change in Step S180, the vehicle starts to run after the gas filling, and during this run, hydrogen gas is first supplied from the hydrogen gas tank 110r that had not been used until then to the fuel cell 100 after the tank is filled. Therefore, once a positive judgment is made in Step S180, the process moves on to Step 120 described later.

Following the positive judgment that the gas filling in Step S105 is complete, the control unit 200 stands by until the state of the gas filled in the hydrogen gas tank 110f expected to operate first stabilizes (Step S110). Thereafter, after the stand-by period, the control unit 200 reads the detected gas pressure of the first gas pressure sensor 131 and second gas pressure sensor 132 and stores the detected gas pressure of the first gas pressure sensor 131 at this time (filled gas pressure Pi) in the given memory area (Step S120). In this case, in Step S120 where a positive judgment was made that; there had been a change in the tank operation in Step S180 described above, the reading of detected gas pressure is performed only for the second gas pressure sensor 132. The two processes before and after the change in the tank operation is described separately in detail below as necessary.

In Step S130 following the sensor reading in Step S120, the gas supply from the hydrogen gas tank 110f is performed for the first time after the gas filling. Since these circumstances are nothing different from those in the first embodiment described above, the control unit 200 calculates the gas pressure differential ΔP between the filled gas pressure Pi detected by the first gas pressure sensor 131 and the initial gas supply pressure Po detected by the second gas pressure sensor 132. Meanwhile, after the change in the tank operation during the running process following the gas filling, the gas from the hydrogen gas tank 110r is supplied for the first time. This situation is assumed to be not reflecting the gas pressure after the gas filling because some time has passed since the gas filling. Therefore, in Step S130 after the operational change to the hydrogen gas tank 110r, the control unit 200 calculates the gas pressure differential ΔP between the filled gas pressure Pi and the initial gas supply pressure Po detected by the second gas pressure sensor 132 using the filled gas pressure Pi already stored in Step S120. Since the hydrogen filling pipeline 120R with the first gas pressure sensor 131 installed therein (see FIG. 1) is in a closed state at the check valves 114f, 114r, the gas pressure detected by the first gas pressure sensor 131 may be handled as the filled gas pressure Pi to calculate the gas pressure differential ΔP even after the operational change to the hydrogen gas tank 110r. Once the gas pressure differential ΔP is calculated, the control unit 200 carries out the process of Steps S130 to S170 in succession as has been done in the embodiment described above.

The fuel cell system 10 of the third embodiment described above stores the gas pressure detected by the first gas pressure sensor 131 (filled gas pressure Pi) when hydrogen gas is filled for operating the two hydrogen gas tanks 110f and 110r to be used for gas supply to the fuel cell 100 (step S120). Then, in the process of gas supply from the hydrogen gas tank 110f that has been operating since the start of gas filling, an output evaluation is made using the sensor output of the second gas pressure sensor 132 that detects the gas pressure of the hydrogen gas tank 110 when hydrogen gas is supplied to the fuel cell 100 based on the gas pressure differential ΔP between the gas pressure detected by the first gas pressure sensor 131 (filled gas pressure Pi) when hydrogen gas is filled and the gas pressure detected by the second gee pressure sensor 132 (initial gas supply pressure P0) (Steps S135 to 170). Meanwhile, when the hydrogen gas tank 110r is operated to be newly used during running of the vehicle after the gas filling and hydrogen gas is first supplied from the hydrogen gas tank 110r to the fuel cell 100, an output evaluation is performed using the sensor output of the second gas pressure sensor 132 that detects the gas pressure of the hydrogen gas tank 110 during fire gas supply to the fuel cell 100 based on the gas pressure differential ΔP between the gas pressure detected by the second gas pressure sensor 132 (initial gas supply pressure P0) and the gas pressure detected by the first gas pressure sensor 131 (filled gas pressure Pi) (Steps S135 to S170).

Since the hydrogen gas tank 110r that has been newly used during running of the vehicle after the gas filling maintains the gas filling pressure, it supplies hydrogen gas to the fuel cell 100 under this gas filling pressure. That way, the fuel cell system 10 of the present embodiment performs an output evaluation after the gas filling using the gas pressure detected by the second gas pressure sensor 132 during the initial supply of hydrogen gas from the hydrogen gas tank 110f, which is the primary tank to be operated after the gas filling, and the initial supply of hydrogen gas from the hydrogen gas tank 110r, which has been newly used. Therefore, according to the fuel cell system 10 of the present embodiment, by means of increasing the frequency of carrying out the output evaluation using the sensor output of the second gas pressure sensor 132 that detects the gas pressure supplied to the fuel cell 100, deterioration of reliability in the output evaluation is prevented more effectively.

Figure 5:
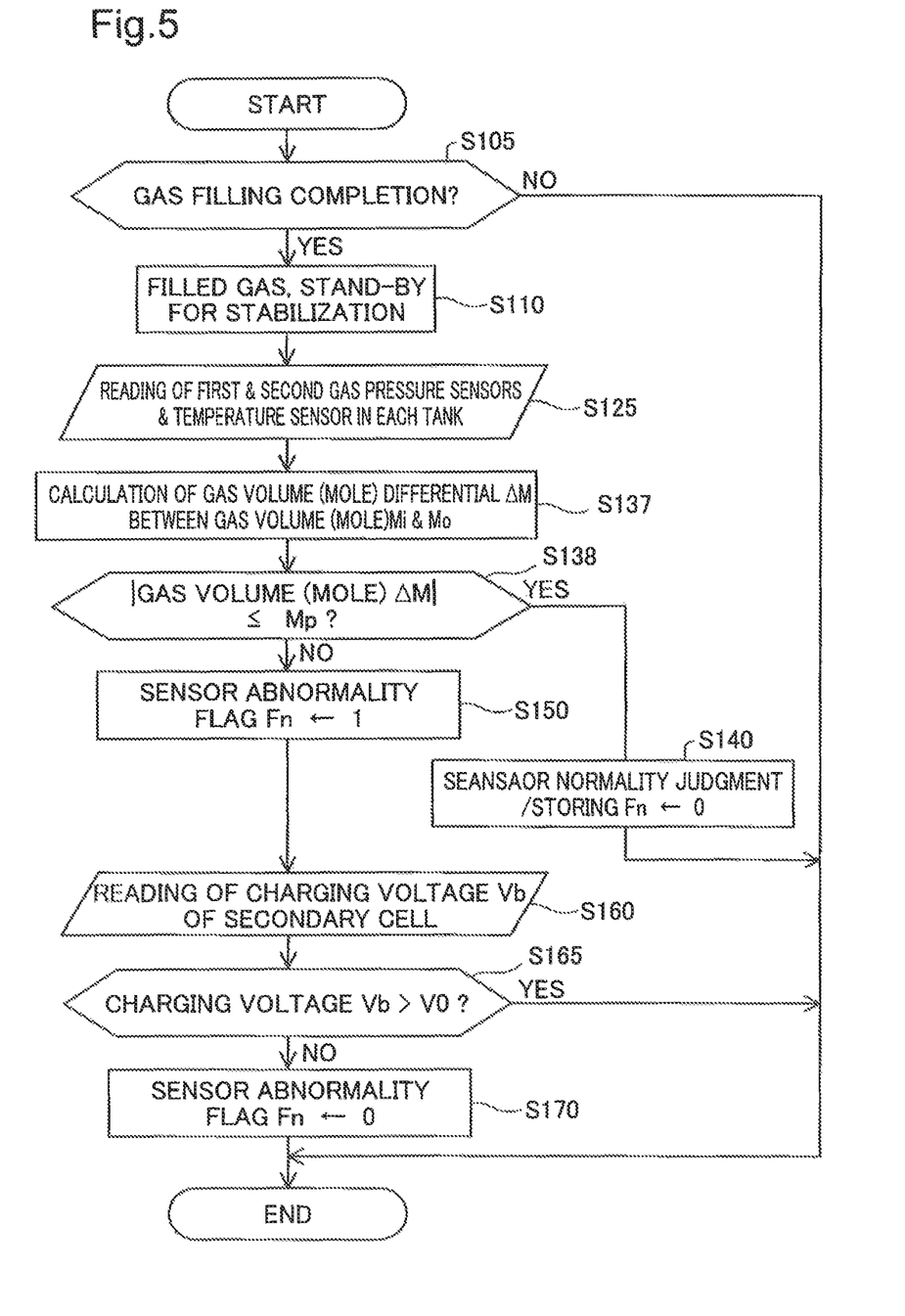
FIG. 5 is a flow chart showing an output evaluation process of the pressure sensor according to the fourth embodiment.

FIG. 3 is a flow chart showing an output evaluation process of the pressure sensor according to the fourth embodiment. This embodiment is characterized by the output evaluation based on the gas volume (mole) differential ΔM equivalent to the gas pressure differential ΔP. The gas pressure differential ΔP is calculated from the filled gas pressure Pi and the initial gas supply pressure P0, and these pressures Pi and Po turn out to be the gas pressure in a closed space including the filling-side tank pipelines 117f, 117r downstream from the filling-side manifold 123 of FIG. 1, each of the hydrogen gas tank 110, and supply-side tank pipelines 116f, 116r extending from each tank to the supply-side manifold 121. The volume (mole) of gas contained in the closed space of a given volume, such as the hydrogen gas tank, is calculated from the gas pressure (filled gas pressure Pi or initial gas supply pressure P0) and the gas temperature in accordance with the equation of gas state. Since the gas temperature in this case is determined by the temperature sensors 115f, 115r is the hydrogen gas tanks 110f, 110r, the filled gas pressure Pi detected by the first gas pressure sensor 131 and the gas volume (mole) obtained from the failed gas pressure Pi and temperatures detected by the temperature sensors 115f, 115r in accordance with the equation of gas state become equivalent to each other for the purpose of defining the state of hydrogen gas. The same holds true for the initial gas supply pressure Po and the gas pressure differential ΔP.

Thus, the tank device using the gas volume (mole) differential ΔM is configured to calculate the filling hydrogen gas volume of the hydrogen gas tank 110 during the gas filling in the hydrogen gas tank 110, which is a fuel gas tank that stores fuel gas to be supplied to the gas consuming device such as the fuel cell 100, based on the hydrogen gas tank 110, the first gas pressure sensor 131 that detects the gas pressure of the hydrogen gas tank 110, the second gas pressure sensor 132 that detects the gas pressure of the hydrogen gas to be supplied from the hydrogen gas tank 110 to the fuel cell 100 in the gas supply pipeline extending from the hydrogen gas tank 110 to the fuel cell 100, and the in-tank temperature obtained from the gas pressure detected by the first gas pressure sensor and the temperature sensors 115f, 115r, and at the same time, calculate the earliest hydrogen gas supply volume of the hydrogen gas tank 110 during the initial gas supply to the fuel cell 100 based on the gas pressure detected by the second gas pressure sensor 132 and the temperature sensors 110f, 110r, and make a judgment of no output failure in either of the first gas pressure sensor 131 and second gas pressure sensor 132, if the gas volume differential between the filling hydrogen gas volume and the earliest hydrogen gas supply volume is within a given threshold value.

Then, in the tank device 1 with the configuration described above and also in the output evaluation process of the fuel cell system 10 shown in FIG. 5, the control unit 200 performs the process of judgment on the completion of gas filling (Step S105) and toe following process as has been done in the output evaluation process of the embodiment described at the very beginning, and in Step S125 after the stand-by for gas stabilization, reads the temperature in the hydrogen gas tanks 110f, 110r detected by the temperature sensors 115f, 115r in addition to the gas pressure detected by the first and second gas pressure sensors 131, 132. In the subsequent Step S137, the control unit 200 calculates the gas volume (mole) differential ΔM between the gas volume (mole) Mi obtained from the filled gas pressure Pi and temperatures detected by the temperature sensor 115f, 115r in accordance with the equation of gas state and the gas volume (mole) M0 obtained front the initial gas supply pressure Po and temperatures detected by the temperature sensors 115f, 115r. The control tin it 200 compares the gas volume (mole) differential ΔM obtained as described above with a threshold value Mp that is equivalent to the above threshold αp (Step S138), and in response to the results thereof, carries out the process of Steps S140 to S170. Deterioration of reliability in the output evaluation using the first and second gas pressure sensors 131, 132 are prevented also by this tank device 1 of the fuel cell system 10 of the fifth embodiment.

The present invention is not limited to the embodiments described above and is implemented in various configurations within the ramie not to deviate from the spirit of the invention. For example, the technical characteristics of the embodiments corresponding to those in each aspect described in the Disclosure of the Invention is replaced or combined as appropriate in order to achieve the whole or part of the effects described above. Also, if those technical characteristics are not described as essential in this specification, they are deleted as appropriate.

For example, in the embodiments described above, the two hydrogen gas tanks were mounted on the vehicle in the front-rear direction, but the vehicle can take a configuration of a single hydrogen gas tank or three or more hydrogen gas tanks on board. Further, the tanks are mounted not only in the front-rear direction but also in the left-right direction of the vehicle. As to the first and second gas pressure sensors 131, 132, at least one of them may be installed in each hydrogen gas tank.

The above embodiments nave been described as the tank device 1 installed in the fuel cell system 10 that supplies hydrogen gas to the fuel cell 100, but they may be applied to a tank, device and a gas supply system that supply natural gas to an internal combustion engine that operates with the combustion energy of natural gas, or to a tank, device in so-called a natural gas vehicle and the like. Also, they may be applied as a tank device in a power generation system where the fuel cell 100 is installed in place in a building to generate power and the power generating system using seen a tank device. The invention may be materialized as a gas tank device or a gas supply device for a gas consuming device different from the fuel cell 100.

Also, in the output evaluation process of FIGS. 3, 4 in the second and third embodiments, respectively, a gas volume (mole) differential ΔM may be determined to perform the output evaluation based on such a differential ΔM. The invention may be applied as another type of gas consuming device different from the fuel cell 100. In the above embodiments, the control unit 200 executes the processes to calculate, evaluate, or judge by the steps or program. The control unit 200 may be configured to use circuitry that materializes these processes in whole or part.

What is claimed is:

1. A tank device comprising:
   a fuel gas tank that stores fuel gas to be supplied to a gas consuming device;
   a first pressure sensor that detects the gas pressure when the fuel gas is filled in the fuel gas tank;
   a second pressure sensor that detects the as pressure of the fuel gas to be supplied from the fuel gas tank to the gas consuming device in a gas supply pipeline extending from the fuel gas tank to the gas consuming device;
   a sensor output evaluation unit that determines a gas pressure differential between the gas pressure detected by the first pressure sensor when fuel gas tank is filled with gas and the gas pressure detected by the second pressure sensor when fuel gas is first supplied from the fuel gas tank to the gas consuming device after the gas filling, and makes a judgment that there is not an output abnormality in any of the first and second pressure sensors if the gas pressure differential is within a given threshold value, and makes a judgment that there is an output abnormality in either of the first and second pressure sensors if the gas pressure differential is beyond the given threshold value; and
   multiple fuel gas tanks and a tank operation unit that operates to use the multiple fuel gas tanks in sequence for supplying gas to the gas consuming device, wherein
   the sensor output evaluation unit stores the gas pressure detected by the first pressure sensor when the fuel gas tank is fill up, determines a gas pressure differential between the gas pressure detected by the first gas pressure sensor that has been stored and the gas pressure detected by the second gas pressure sensor when the fuel gas is supplied from the fuel gas tank to the gas consuming device after the gas filling, the fuel gas tank is started to use for gas supply by the tank operation unit, and makes a judgment of no output abnormality in any of the first pressure sensor and second pressure sensor if the gas pressure differential is within a given threshold value.

2. The tank device in accordance with claim 1, wherein the first pressure sensor detects the gas pressure of the fuel gas in the gas filling pipeline for filling gas in the fuel gas tank under a closed condition of a receptacle of a gas filling nozzle installed at one end of the pipeline.

3. A vehicle comprising:
   the tank device in accordance with claim 2; and
   a battery that is charged by electric power generated in a fuel cell using the fuel gas supplied from the fuel gas tank.

4. The tank device in accordance with claim 1, wherein the gas consuming device is a fuel cell.

5. A vehicle comprising:
   the tank device in accordance with claim 4; and
   a battery that is charged by electric power generated in the fuel cell using the fuel gas supplied from the fuel gas tank.

6. A vehicle comprising:
   the tank device in accordance with claim 1; and
   a battery that is charged by electric power generated in a fuel cell using the fuel gas supplied from the fuel gas tank.

7. A tank device comprising:
   a fuel gas tank that stores fuel gas to be supplied to a gas consuming device;
   a first pressure sensor that detects the gas pressure when the fuel gas is filled in the fuel gas tank;
   a second pressure sensor that detects the gas pressure of the fuel as to be sup lied from the fuel gas tank to the gas consuming device in a gas supply pipeline extending from the fuel gas tank to the gas consuming device;
   a sensor output evaluation unit that determines a gas pressure differential between the gas pressure detected by the first pressure sensor when fuel gas tank is filled with gas and the gas pressure detected by the second pressure sensor when fuel gas is first supplied from the fuel gas tank to the gas consuming device after the gas filling, and makes a judgment that there is not an output abnormality in any of the first and second pressure sensors if the gas pressure differential is within a given threshold value, and makes a judgment that there is an output abnormality in either of the first and second pressure sensors if the gas pressure differential is beyond the given threshold value; and
   a battery supplying an electric power to the first and second pressure sensors,
   wherein the sensor output evaluation unit does not make any judgment on the output abnormality using the detected gas pressure or clears the judgment of the output abnormality made by using the detected gas pressure, under a situation where an output voltage of the battery is lower than a predetermined voltage.

8. A vehicle comprising:
   the tank device in accordance with claim 7; and
   a battery that is charged by electric power generated in a fuel cell using the fuel gas supplied from the fuel gas tank.

9. The tank device in accordance with claim 7, wherein the first pressure sensor detects the gas pressure of the fuel gas in the gas filling-pipeline for filling gas in the fuel gas tank under a closed condition of a receptacle of a gas filling nozzle installed at one end of the pipeline.

10. The tank device in accordance with claim 7, wherein the gas consuming device is a fuel cell.

11. A tank device comprising:
    a fuel gas tank that stores fuel gas to be supplied to a gas consuming device;
    a first pressure sensor that detects a gas pressure when the fuel gas is filled in the fuel gas tank;
    a first temperature sensor that detects a fuel gas temperature in the fuel gas tank when the fuel gas tank is filled;
    a second gas pressure sensor that detects a pressure of the fuel gas to be supplied from the fuel gas tank to the gas consuming device in a gas supply pipeline extending from the fuel gas tank to the gas consuming device;
    a second temperature sensor that detects a fuel gas temperature in the fuel gas tank when the fuel gas is supplied to the gas consuming device; and a sensor output evaluation unit that determines a gas volume differential between a gas volume in the fuel gas tank obtained from the gas pressure detected by the first pressure sensor when gas is filled in the fuel gas tank and the temperature detected by the first temperature sensor and a gas volume in the fuel gas tank obtained from the gas pressure detected by the second pressure sensor when the fuel gas is first supplied from the fuel gas tank to the gas consuming device after the gas filling and the temperature detected by the second temperature sensor, makes a judgment that is not an output abnormality in any of the first and second pressure sensors if the gas volume differential is within a given threshold value, and makes a judgment that there is an output abnormality in at least one of the first and second pressure sensors if the gas volume differential is beyond the given threshold value.

12. An output evaluation method of a pressure sensor used for detecting a pressure in a fuel gas tank that stores fuel gas to be supplied to a gas consuming device, comprising:
obtaining a first fuel gas pressure of the fuel gas tank detected by a first pressure sensor, the first fuel gas pressure being the fuel gas pressure in the fuel gas tank when the fuel gas tank is filled;
obtaining a second fuel gas pressure of the fuel gas tank when the fuel gas is first supplied from the fuel gas tank to a gas consuming device after the fuel gas filling, by detecting the fuel gas pressure in a gas supply pipeline extending from the fuel gas tank to the gas consuming device by a second pressure sensor;
determining a gas pressure differential between the first fuel gas pressure obtained and the second fuel gas pressure obtained, and making a judgment that there is not an output abnormality in any of the first and second pressure sensors if the gas pressure differential is within a given threshold value, and making a judgment that there is an output abnormality in at least one of the first and second pressure sensors if the gas pressure differential is beyond the given threshold value; and
using multiple fuel gas tanks to be operated in sequence for supplying gas to the gas consuming device,
wherein the making the judgment on the output abnormality of the first and second pressure sensors comprises:
storing data on the first fuel gas pressure detected by the first pressure sensor when gas is filled in the fuel gas tank;
determining the gas pressure differential between the first fuel gas pressure detected by the first pressure sensor and stored in memory and the second fuel gas pressure detected by the second pressure sensor when the fuel gas is first supplied from the fuel gas tank that is started to use due to the operation of the multiple gas tanks to the gas consuming device after the gas filling; and
making a judgment of no output abnormality in any of the first and second pressure sensors if the gas pressure differential is within a given threshold value.

13. The method in accordance with claim 12, wherein the obtaining the first fuel gas pressure of the fuel gas tank comprises detecting the gas pressure of the fuel gas tank in the gas supply pipeline for filling gas in the fuel gas tank under a closed condition of a receptacle of a gas filling nozzle installed at one end of the pipeline.

14. The method in accordance with claim 12, wherein the gas consuming device is a fuel cell.

15. An output evaluation method of a pressure sensor used for detecting a pressure in a fuel gas tank that stores fuel gas to be supplied to a gas consuming device, comprising:
obtaining a first fuel gas pressure of the fuel gas tank detected by a first pressure sensor, the first fuel gas pressure being the fuel gas pressure in the fuel gas tank when the fuel gas tank is filled;
obtaining a second fuel gas pressure of the fuel gas tank when the fuel gas is first supplied from the fuel gas tank to a gas consuming device after the fuel gas filling, by detecting the fuel gas pressure in a gas supply pipeline extending from the fuel gas tank to the gas consuming device by a second pressure sensor;
determining a gas pressure differential between the first fuel gas pressure obtained and the second fuel gas pressure obtained, and making a judgment that there is not an output abnormality in any of the first and second pressure sensors if the gas pressure differential is within a given threshold value, and making a judgment that there is an output abnormality in at least one of the first and second pressure sensors if the gas pressure differential is beyond the given threshold value; and
providing a battery supplying an electric power to the first and second pressure sensors,
wherein under a situation where an output voltage of the battery is lower than a predetermined voltage, any judgment on the output abnormality using the detected gas pressure is not executed, or the judgment of the output abnormality made by using the detected gas pressure is cleared.

16. The method in accordance with claim 15, wherein the obtaining the first fuel gas pressure of the fuel gas tank comprises detecting the gas pressure of the fuel gas tank in the gas supply pipeline for filling gas in the fuel gas tank under a closed condition of a receptacle of a gas filling nozzle installed at one end of the pipeline.

17. The method in accordance with claim 15, wherein the gas consuming device is a fuel cell.

18. An output evaluation method of a pressure sensor used for detecting a pressure in a fuel gas tank that stores fuel gas to be supplied to a gas consuming device, comprising:
obtaining a first fuel gas pressure of the fuel gas tank by detecting, by a first pressure sensor, the gas pressure in the fuel gas tank when it is filled;
detecting a first temperature of the fuel gas in the fuel gas tank when it is filled;
obtaining a second fuel gas pressure of the fuel gas tank by detecting the fuel gas pressure of the fuel gas tank by a second pressure sensor in a gas supply pipeline extending from the fuel gas tank to the gas consuming device when the fuel gas is first supplied from the fuel gas tank to the gas consuming device after the gas filling;
detecting a second temperature of the fuel gas in the fuel gas tank when the fuel gas is supplied to the gas consuming device; and
determining a gas volume differential between a gas volume in the fuel gas tank obtained from the first fuel gas pressure and the first temperature of the fuel gas tank and a gas volume in the fuel gas tank obtained from the second fuel gas pressure and the second temperature of the fuel gas tank, making a judgment that there is not an output abnormality in any of the first and second pressure sensors if the gas volume differential is within a given threshold value, and making a judgment that there is an output abnormality in at least one of the first and second pressure sensors if the gas volume differential is beyond the given threshold value.

* * * * *